US00PP23799P3

(12) United States Plant Patent
Zaiger et al.

(10) Patent No.: US PP23,799 P3
(45) Date of Patent: Aug. 6, 2013

(54) PEACH TREE NAMED 'SITKA'

(50) Latin Name: *Prunus persica*
Varietal Denomination: Sitka

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 112 days.

(21) Appl. No.: 13/373,515

(22) Filed: Nov. 17, 2011

(65) Prior Publication Data

US 2013/0133114 P1 May 23, 2013

(51) Int. Cl.
*A01H 5/00* (2006.01)

(52) U.S. Cl.
USPC ..... Plt./195

(58) Field of Classification Search
USPC ..... Plt./195
See application file for complete search history.

*Primary Examiner* — June Hwu

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree being a regular and productive bearer of large size fruit.
2. The tree with vigorous, upright growth.
3. Producing fruit with a high degree of attractive red-orange skin color.
4. White flesh fruit with good flavor and eating quality.
5. Producing fruit with mild, sweet, low acid flavor.

1 Drawing Sheet

Botanical designation: *Prunus persica.*
Variety denomination: 'Sitka'.

BACKGROUND OF THE VARIETY

Field of the Invention

In the field of plant genetics, we conduct an extensive and continuing plant-breeding program including the organization and asexual reproduction of orchard trees, and of which, plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, are 'Spring Snow' Peach (U.S. Plant Pat. No. 9,883) and the (non-patented) proprietary seedling selections '172LE55', '54Z432', '36EB86', '5GE8' and '3LG573'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from seed of a first generation cross between our two proprietary non-patented peach seedlings '172LE55' and '54Z432'. The seed parent '172LE55' (non-patented) originated from a cross between our proprietary (non-patented) peach seedlings '36EB86' and '5GE8'. The pollen parent '54Z432' (non-patented) originated from an open pollinated proprietary nectarine seedling '3LG573' (non-patented). A large number of seeds from this first generation cross were grown on their own root system. Under close and careful observation, one such seedling, which is the present variety, exhibited desirable tree and fruit characteristics and was selected in 2001 for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous upright growth and a productive and regular bearer of large size, white flesh, clingstone fruit with a mild, sweet, low acid flavor and good eating quality. The fruit is further characterized by having an attractive red-orange skin color, being relatively uniform in size throughout the tree and holding firm on the tree 2 weeks after maturity (shipping ripe). In comparison to its proprietary peach seed parent '172LE55' (non-patented) the fruit of the new variety has firmer flesh and is approximately 1 week later in maturity.

In comparison to its proprietary peach pollen parent '54Z432' (non-patented) the fruit of the new variety has white flesh compared to yellow and is approximately 10 days later in maturity. In comparison to the commercial peach variety 'Spring Snow' (U.S. Plant Pat. No. 9,883) the fruit of the new variety has a greater degree of red skin color and is approximately 5 days later in maturity.

PHOTOGRAPH OF THE VARIETY

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from an 8 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 8 year old specimens grown near Modesto, Calif., with color in accordance with Munsell Book of Color.

Tree:

*Size.*—Large, normally pruned to 3 to 3.5 meters in height and width for economical harvesting of fruit.

*Vigor.*—Vigorous, growth of 1.5 to 2 meters in height the first growing season. Varies with soil type, fertility of soil and climatic conditions.

*Form.*—Upright, usually pruned to vase shape.

*Branching habit.*—Crotch angle approximately 35°, increases with heavy crop load.

*Productivity.*—Productive, fruit thinning and spacing necessary for desired market size. Fruit set varies with climatic conditions during bloom season.

*Bearer.*—Regular, adequate fruit set for 6 consecutive years. No alternate bearing observed.

*Fertility.*—Self fertile.

*Density.*—Medium dense, usually pruned to vase shape to allow more sunlight to center of tree to enhance fruit color and health of fruit wood.

*Hardiness.*—Hardy in all stone fruit growing areas of California. Tree grown in USDA Hardiness Zone 9. Winter chilling requirement approximately 500 hours at or below 45° F.

Trunk:

*Size.*—Medium. Average circumference 38.1 cm at 35.6 cm above ground on a 8 year old tree.

*Stocky.*—Medium stocky.

*Texture.*—Medium shaggy, roughness increases with age.

*Color.*—Varies from 10YR 3/2 to 2.5Y 3/4.

Branches:

*Size.*—Medium. Average circumference 15.5 cm at 1.2 meters above ground. Crotch angle approximately 35°, increases with heavy crop load.

*Surface texture.*—New growth relatively smooth. Mature growth medium rough, roughness increases with age.

*Lenticels.*—Size — medium. Average length 3.2 mm. Average width 2.1 mm. Color varies from 10YR 5/8 to 10YR 5/10. Average number 23 in a 25.8 sq cm area.

*Color.*—New growth varies from 5GY 6/6 to 7.5YR 4/4. Mature growth varies from 10YR 3/4 to 2.5YR 3/4, varies with age of growth.

Leaves:

*Size.*—Large. Average length 141.6 mm. Average width 40.0 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slightly indented over midrib and leaf veins, glabrous. Lower surface relatively smooth except for small ridges created by midrib and pinnate venation, glabrous.

*Petiole.*—Average length 9.5 mm. Average width 1.8 mm. Color varies from 5GY 6/6 to 5GY 5/8. Longitudinally grooved. Surface — glabrous.

*Glands.*—Type — reniform. Size — small. Average length 0.9 mm. Average diameter 0.5 mm. Average number 1, varies from 0 to 2. Located primarily on base of leaf blade and upper portion of petiole. Color varies from 2.5GY 6/6 to 5GY 6/6.

*Stipules.*—Average length 9.1 mm. Average number — 2. Margin — pectinate. Color varies from 5GY 6/6 to 5GY 5/6.

*Color.*—Upper surface varies from 7.5GY 2/2 to 7.5GY 2/4. Lower surface varies from 7.5GY 3/4 to 7.5GY 4/4. Midvein color varies from 10Y 8/2 to 2.5GY 8/2.

Flower buds:

*Size.*—Large. Average length 14.8 mm. Average diameter 10.0 mm.

*Hardiness.*—Hardy, with respect to California winters.

*Form.*—Plump, conical, becoming elongated before opening.

*Pedicel.*—Average length 4.7 mm. Average width 1.4 mm. Color varies from 2.5GY 7/8 to 7.5R 3/8.

*Color.*—Varies from 5RP 7/8 to 7.5RP 8/6.

Flowers:

*Date of first bloom.*—Feb. 14, 2011.

*Date of petal fall.*—Feb. 24, 2011, varies slightly with climatic conditions.

*Size.*—Large, showy. Average height 19.5 mm. Average diameter 39.9 mm.

*Petals.*—Number — normally 5, alternately arranged to sepals. Size — large. Average length 20.6 mm. Average width 15.9 mm. Form — nearly globose, base narrows at point of attachment. Margin — sinuate. Color varies from 5RP 8/4 to 5RP 8/6. Both upper and lower surfaces glabrous.

*Sepals.*—Number — normally 5, alternately arranged to petals. Size — large. Average length 6.2 mm. Average width 5.4 mm. Shape — triangular. Margin — entire. Upper surface glabrous. Lower surface pubescent. Color — upper surface varies from 5GY 7/8 to 5GY 6/8. Lower surface varies from 7.5R 2/8 to 7.5R 3/6.

*Stamens.*—Average number per flower 41. Filament color varies from N 9.5/ (white) to 10P 9/2 in older flowers. Anther color varies from 10R 2/6 to 2.5Y 8/10.

*Pollen.*—Self fertile. Color varies from 2.5GY 6/8 to 2.5Y 8/10.

*Pistil.*—Number — normally one. Surface — pubescent. Average length 17.2 mm. Position of stigma average of 1.1 mm below anthers. Color varies from 7.5Y 8/10 to 7.5Y 8/8.

*Fragrance.*—Moderate aroma.

*Color.*—Varies from 5RP 8/4 to 5RP 8/6.

*Number flowers per bud.*—One.

*Pedicel.*—Average length 4.7 mm. Average width 1.5 mm. Color varies from 2.5GY 6/6 to 5GY 7/8.

Fruit:

*Maturity when described.*—Firm ripe.

*Date of first picking.*—May 30, 2011.

*Date of last picking.*—Jun. 6, 2011, varies slightly with climatic conditions.

*Size.*—Large. Average diameter axially 59.5 mm. Average transversely in suture plane 69.3 mm. Average weight 173.2 grams, average weight varies slightly with fertility of the soil, amount of thinning and climatic conditions.

*Form.*—Globose.

*Suture.*—Nearly smooth.

*Ventral surface.*—Nearly smooth.

*Apex.*—Slightly retuse.

*Base.*—Flat to slightly retuse.

*Stem cavity.*—Rounded to slightly elongated in suture plane. Average depth 8.4 mm. Average diameter 8.2 mm.

Stem:

*Size.*—Small. Average length 8.9 mm. Average diameter 3.7 mm.

*Color.*—Varies from 5GY 6/8 to 5GY 5/8.

Flesh:

*Ripens.*—Evenly.

*Texture.*—Firm, meaty.

*Fibers.*—Few, small, tender.

*Firmness.*—Good, comparable to 'Spring Snow' Peach (U.S. Plant Pat. No. 9,883).

*Aroma.*—Moderate.

*Amydgalin.*—Undetected.

*Eating quality.*—Good.

*Flavor.*—Good, mild, sweet, low acid flavor.

*Juice.*—Heavy amount, enhances flavor.

*Brix.*—Average 11.0°, varies slightly with amount of fruit per tree and climatic conditions.

*Color.*—Varies from N 9.5/ (white) to 2.5Y 9/2.

*Pit cavity.*—Average length 33.5 mm. Average width 24.0 mm. Average depth 11.0 mm. Color varies from 2.5GY 8/4 to 7.5GY 8/4.

Skin:

*Thickness.*—Medium.

*Surface.*—Smooth (no dimples or ripples).

*Pubescence.*—Moderate amount.

*Tendency to crack.*—None.

*Color.*—Ground color pale yellow, varies from 10YR 9/2 to 2.5Y 9/2. Overspread with 5R 3/8 to 5R 2/2.

*Tenacity.*—Tenacious to flesh.

*Astringency.*—Undetected.

Stone:

*Type.*—Clingstone.

*Size.*—Large. Average length 32.8 mm. Average width 23.5 mm. Average thickness 21.3 mm.

*Form.*—Ovoid.

*Base.*—Varies from round to flat.

*Apex.*—Pointed. Average length 2.6 mm.

*Surface.*—Pitted throughout, pits vary from round to elongated.

*Sides.*—Unequal, one side extending further from suture plane.

*Ridges.*—Relatively smooth, extending from base toward apex.

*Tendency to split.*—Slight.

*Color.*—Varies from 10YR 6/6 to 10YR 6/8, when dry.

Kernel:

*Size.*—Medium to large. Average length 16.4 mm. Average width 10.8 mm. Average depth 7.4 mm.

*Form.*—Ovoid.

*Viability.*—Partially viable, incomplete embryo development.

*Skin.*—Color varies from 7.5Y 9/4 to 10Y 9/2.

Use: Dessert.

*Market.*—Local and long distance.

Keeping quality: Good, held firm in cold storage at 38° to 42° F. for 2 weeks without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

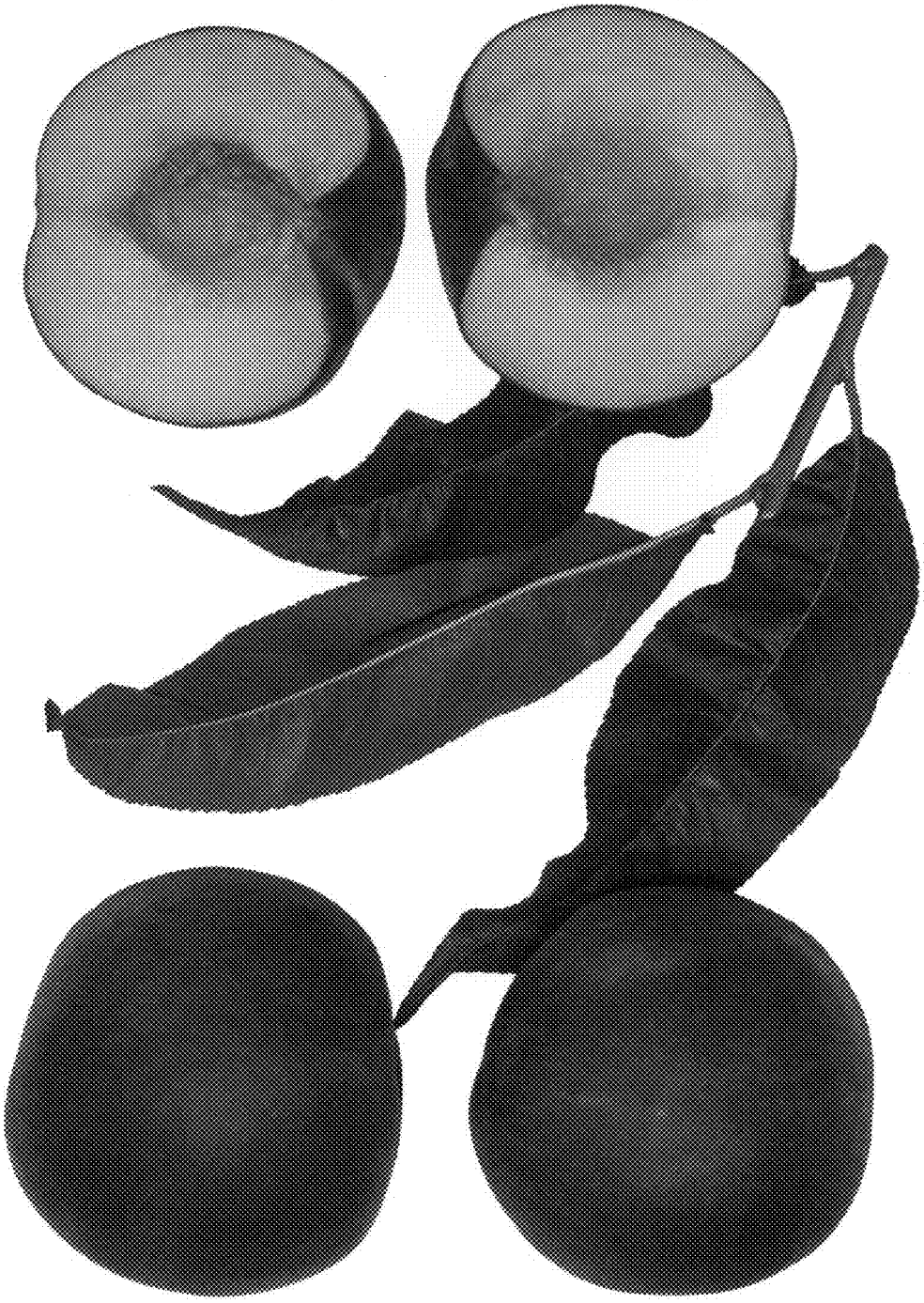

* * * * *